United States Patent
Dunkel et al.

(10) Patent No.: US 7,381,688 B2
(45) Date of Patent: Jun. 3, 2008

(54) METHYLTHIOPHENE CARBOXANILIDES

(75) Inventors: Ralf Dunkel, Monheim (DE); Heiko Rieck, Foy lés Lyon (FR); Hans-Ludwig Elbe, Wuppertal (DE); Ulrike Wachendorff-Neumann, Neuwied (DE); Astrid Mauler-Machnik, Leichlingen (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 387 days.

(21) Appl. No.: 10/511,742

(22) PCT Filed: Apr. 15, 2003

(86) PCT No.: PCT/EP03/03894

§ 371 (c)(1),
(2), (4) Date: Nov. 17, 2005

(87) PCT Pub. No.: WO03/091240

PCT Pub. Date: Nov. 6, 2003

(65) Prior Publication Data

US 2006/0148886 A1 Jul. 6, 2006

(30) Foreign Application Priority Data

Apr. 24, 2002 (DE) .................. 102 18 231

(51) Int. Cl.
*A01N 43/10* (2006.01)
*C07D 333/04* (2006.01)

(52) U.S. Cl. .................. 504/289; 549/29; 549/70; 549/72; 504/288

(58) Field of Classification Search .................. 549/29, 549/70, 72; 504/288, 289
See application file for complete search history.

(56) References Cited

U.S. PATENT DOCUMENTS

| | | | | |
|---|---|---|---|---|
| 3,892,775 A * | 7/1975 | Kobzina | ...................... | 549/72 |
| 5,330,995 A | 7/1994 | Eicken et al. | ................ | 514/355 |
| 5,438,070 A | 8/1995 | Eicken et al. | ................ | 514/403 |
| 5,480,897 A | 1/1996 | Eicken et al. | ................ | 514/365 |
| 5,556,988 A | 9/1996 | Eicken et al. | ............ | 548/374.1 |
| 5,589,493 A | 12/1996 | Eicken et al. | ................ | 514/355 |
| 5,801,122 A * | 9/1998 | Takematsu et al. | .......... | 504/289 |
| 5,922,732 A | 7/1999 | Urch et al. | .................. | 514/304 |
| 5,968,947 A | 10/1999 | Urch et al. | .................. | 514/299 |
| 6,093,726 A | 7/2000 | Urch et al. | .................. | 514/299 |
| 6,174,894 B1 | 1/2001 | Urch et al. | .................. | 514/299 |
| 6,177,442 B1 | 1/2001 | Urch et al. | .................. | 514/299 |
| 6,207,676 B1 | 3/2001 | Urch et al. | .................. | 514/304 |
| 6,291,474 B1 | 9/2001 | Brightwell et al. | .......... | 514/299 |
| 6,369,093 B1 | 4/2002 | Elbe et al. | .................. | 514/406 |
| 6,391,883 B1 | 5/2002 | Urch et al. | .................. | 514/255 |
| 7,176,228 B2 * | 2/2007 | Elbe et al. | .................. | 514/406 |
| 2002/0061913 A1 | 5/2002 | Urch et al. | .................. | 514/366 |

FOREIGN PATENT DOCUMENTS

| | | |
|---|---|---|
| EP | 0 741 131 | 11/1996 |
| JP | 9-132567 | 5/1997 |
| JP | 2001-72507 | 3/2001 |
| JP | 2001-72510 | 3/2001 |
| WO | 93/11097 | 6/1993 |
| WO | 02/08197 | 1/2002 |

OTHER PUBLICATIONS

Bull Korean Chem. Soc., vol. 21, No. 2, (month unavailable) 2000, pp. 165-166, Nakcheol Jeong et al, "A Facile Preparation of the Fluoroaryl Zinc Halides: an Application to the Synthesis of Diflunisal".

Chem. Pharm. Bull 40(1), (month unavailable) 1992, pp. 240-244, Kiyoshi Taniguchi et al, "New 2-Aryliminoimidazolidines. II $^{1a)}$ Synthesis and Antihypertensive Activity of 2-(Biphenylimino)-imidazolidines".

White, G.A. et al: "Thiophene carboxamide fungicides: structure-activity relationships with the succinate dehydrogenase complex from wild-type and carboxin-resistant mutant strains of *Ustilago maydis*" Pesticide Biochemistry and Physiology (1980), 14(1), 26-40, XP009016749.

White, G.A. et al: "Thiophene carboxamide fungicides: structure-activity relationships with the succinate dehydrogenase complex from wild-type and carboxin-resistant mutant strains of *Aspergillus nidulans*" Pesticide Biochemistry and Physiology (1986), 25(2), 188-204, XP009016748.

* cited by examiner

*Primary Examiner*—Golam M. M. Shameem
(74) *Attorney, Agent, or Firm*—Richard E.L. Henderson

(57) ABSTRACT

This invention relates to novel methylthiophenecarboxanilides of the formula (I)

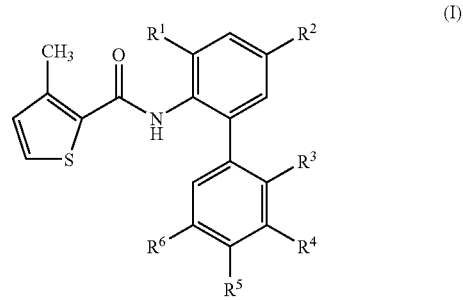

in which
$R^1$, $R^2$, $R^3$, $R^4$, $R^5$ and $R^6$ are as defined in the disclosure, to a plurality of processes for preparing these substances and their use for controlling unwanted microorganisms, and to novel intermediates and their preparations.

7 Claims, No Drawings

METHYLTHIOPHENE CARBOXANILIDES

The present patent application has been filed under 35 U.S.C. 371 as a national stage application of PCT/EP03/03894, filed Apr. 15, 2003, which was published in German as International Patent Publication WO 03/091240 on Nov. 6, 2003, which is entitled to the right of priority of German Patent Application 102 18 231.0, filed Apr. 24, 2002.

The present invention relates to novel methylthiophenecarboxanilides, to a plurality of processes for their preparation and to their use for controlling harmful microorganisms in crop protection and in the protection of materials.

It is already known that numerous carboxanilides have fungicidal properties (cf., for example, WO 93/11097, Can. Pestic. Biochem. Physiol. 1980, 14, 26-40, Can. Pestic. Biochem. Physiol. 1986, 25, 188-204, JP 2001-72507, JP 2001-72510 or EP-A 0 545 099). The activity of the substances described in these publications is good; however, at low application rates it is sometimes unsatisfactory.

This invention now provides novel methylthiophenecarboxanilides of the formula (I)

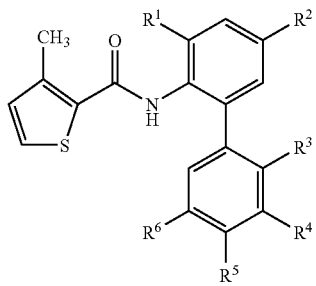

in which
R$^1$ and R$^2$ are identical or different and independently of one another represent hydrogen or fluorine,
R$^3$, R$^4$ and R$^6$ are identical or different and independently of one another represent hydrogen, halogen, C$_1$-C$_6$-alkyl or C$_1$-C$_4$-haloalkyl having 1 to 5 halogen atoms,
R$^5$ represents hydrogen, halogen, cyano, nitro, C$_1$-C$_6$-alkyl, C$_2$-C$_6$-alkenyl, C$_3$-C$_6$-cycloalkyl, C$_1$-C$_4$-alkoxy, C$_1$-C$_4$-alkylthio, C$_1$-C$_4$-alkyl-sulfonyl, C$_1$-C$_4$-haloalkyl having 1 to 5 halogen atoms, C$_1$-C$_4$-haloalkoxy having 1 to 5 halogen atoms, C$_1$-C$_4$-haloalkylthio having 1 to 5 halogen atoms or C$_1$-C$_4$-haloalkylsulfonyl having 1 to 5 halogen atoms, where R$^3$, R$^4$, R$^5$ and R$^6$ do not simultaneously represent hydrogen.

Furthermore, it has been found that methylthiophenecarboxanilides of the formula (I) are obtained by a) reacting methylthiophenecarbonyl halides of the formula (II)

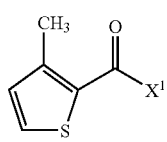

in which
X$^1$ represents halogen
with an aniline derivative of the formula (III)

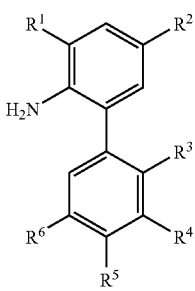

in which
R$^1$, R$^2$, R$^3$, R$^4$, R$^5$ and R$^6$ are as defined above,
if appropriate in the presence of an acid binder and if appropriate in the presence of a diluent, or b) reacting methylthiophenecarboxhaloanilides of the formula (IV)

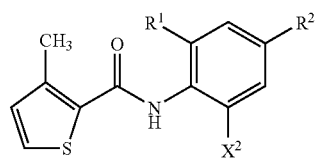

in which
R$^1$ and R$^2$ are as defined above and
X$^2$ represents bromine or iodine,
with a boronic acid of the formula (V)

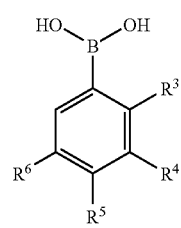

in which
R$^3$, R$^4$, R$^5$ and R$^6$ are as defined above
in the presence of a catalyst, if appropriate in the presence of an acid binder and if appropriate in the presence of a diluent.

Finally, it has been found that the novel methylthiophenecarboxanilides of the formula (I) have very good microbicidal properties and can be used for controlling unwanted micro-organisms both in crop protection and in the protection of materials.

Surprisingly, the methylthiophenecarboxanilides of the formula (I) have considerably better fungicidal activity than the constitutionally more similar active compounds of the prior art having the same direction of action.

The formula (I) provides a general definition of the methylthiophenecarboxanilides according to the invention.

Preference is given to methylthiophenecarboxanilides of the formula (I) in which
- $R^1$ and $R^2$ are identical or different and independently of one another represent hydrogen or fluorine,
- $R^3$, $R^4$ and $R^6$ are identical or different and independently of one another represent hydrogen, fluorine, chlorine, bromine, iodine, methyl, ethyl, n- or i-propyl, n-, i-, s- or t-butyl, trifluoromethyl, trichloromethyl or trifluoroethyl,
- $R^5$ represents hydrogen, fluorine, chlorine, bromine, cyano, nitro, methyl, ethyl, n- or i-propyl, n-, i-, s- or t-butyl, cyclopropyl, methoxy, ethoxy, methylthio, ethylthio, n- or i-propylthio, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio,
- $R^5$ furthermore represents iodine, where $R^3$, $R^4$, $R^5$ and $R^6$ do not simultaneously represent hydrogen.

Particular preference is given to methylthiophenecarboxanilides of the formula (I) in which
- $R^1$ and $R^2$ are identical or different and independently of one another represent hydrogen or fluorine,
- $R^3$, $R^4$ and $R^6$ are identical or different and independently of one another represent hydrogen, fluorine, chlorine, bromine, iodine, methyl or trifluoromethyl,
- $R^5$ represents hydrogen, fluorine, chlorine, bromine, methyl, cyclopropyl, methoxy, methylthio, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio,
- $R^5$ furthermore represents iodine or cyano, where $R^3$, $R^4$, $R^5$ and $R^6$ do not simultaneously represent hydrogen.

Very particular preference is given to compounds of the formula (I) in which $R^1$ and $R^2$ each represent hydrogen.

Very particular preference is given to compounds of the formula (I) in which $R^1$ represents fluorine and $R^2$ represents hydrogen.

Very particular preference is given to compounds of the formula (I) in which $R^1$ represents hydrogen and $R^2$ represents fluorine.

Very particular preference is given to compounds of the formula (I) in which $R^3$, $R^4$ and $R^6$ each represent hydrogen and $R^5$ does not represent hydrogen.

Very particular preference is given to compounds of the formula (I) in which $R^3$ and $R^6$ each represent hydrogen and $R^4$ and $R^5$ each do not represent hydrogen.

Very particular preference is given to compounds of the formula (I) in which $R^4$ and $R^6$ each represent hydrogen and $R^3$ and $R^5$ each do not represent hydrogen.

Very particular preference is given to compounds of the formula (I) in which $R^3$ and $R^5$ each represent hydrogen and $R^4$ and $R^6$ each do not represent hydrogen.

Very particular preference is furthermore given to compounds of the formula (I-a)

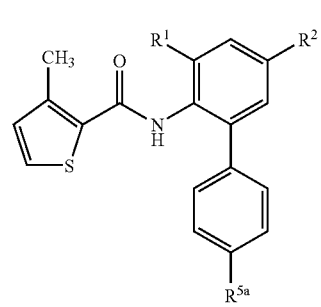

in which
$R^1$ and $R^2$ are as defined above and
$R^{5a}$ represents fluorine, chlorine, bromine, methyl, methylthio, trifluoromethyl, trifluoromethoxy, or trifluoromethylthio,
$R^{5a}$ furthermore represents iodine or cyano.

Especially preferred are compounds of the formula (I-a), in which $R^1$ and $R^2$ each represent hydrogen.

Very particular preference is furthermore given to compounds of the formula (I-b)

(I-b)

in which
$R^1$ and $R^2$ are as defined above,
$R^{4b}$ represents fluorine, chlorine, bromine, methyl or trifluoromethyl and
$R^{5b}$ represents fluorine, chlorine, bromine, methyl, trifluoromethyl, trifluoromethoxy or trifluoromethylthio.

Especially preferred are compounds of the formula (I-b) in which $R^1$ and $R^2$ each represent hydrogen.

Very particular preference is furthermore given to compounds of the formula (I-c)

(I-c)

in which

R$^1$ and R$^2$ are as defined above,

R$^{3c}$ represents fluorine, chlorine, bromine or methyl and

R$^{5c}$ represents fluorine, chlorine, methyl, trifluoromethyl, trifluoromethoxy or trifluoromethylthio.

Especially preferred are compounds of the formula (I-c) in which R$^1$ and R$^2$ each represent hydrogen.

Very particular preference is furthermore given to compounds of the formula (I-d)

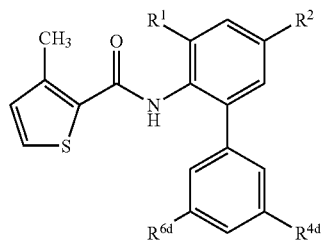

(I-d)

in which

R$^1$ and R$^2$ are as defined above,

R$^{4d}$ represents fluorine or chlorine and

R$^{6d}$ represents fluorine, chlorine, trifluoromethyl or trifluoromethoxy.

Especially preferred are compounds of the formula (I-d) in which R$^1$ and R$^2$ each represent hydrogen.

The general or preferred radical definitions or illustrations given above can also be combined with one another as desired, i.e. between respective ranges and preferred ranges. The definitions apply both to the end products and, correspondingly, to precursors and intermediates. Moreover, individual definitions may not apply.

Saturated hydrocarbon radicals, such as alkyl, can in each case be straight-chain or branched as far as this is possible, including in combination with hetero atoms, such as, for example, in alkoxy.

Halogen-substituted radicals, for example haloalkyl, are mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Using, for example, 3-methyl-2-thiophenecarbonyl chloride and 3'-chloro-4'-fluoro-1,1'-biphenyl-2-amine as starting materials and a base, the course of the process (a) according to the invention can be illustrated by the formula scheme below:

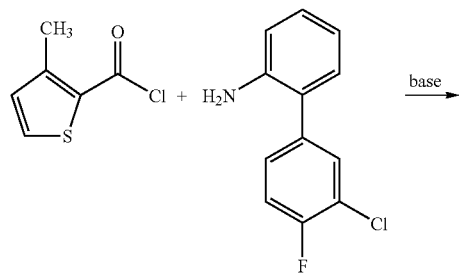

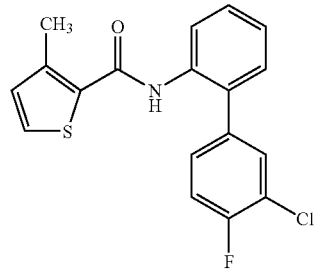

The formula (II) provides a general definition of the methylthiophenecarbonyl halides required as starting materials for carrying out the process (a) according to the invention. In this formula (II), X$^1$ preferably represents chlorine.

The methylthiophenecarbonyl halides of the formula (II) are known, available laboratory chemicals.

The formula (III) provides a general definition of the aniline derivatives furthermore required as starting materials for carrying out the process (a) according to the invention. In this formula (III), R$^1$, R$^2$, R$^3$, R$^4$, R$^5$ and R$^6$ preferably or particularly preferably have those meanings which have already been mentioned in connection with the description of the compounds of the formula (I) according to the invention as being preferred or particularly preferred for these radicals.

The aniline derivatives of the formula (III) are known and/or can be prepared by known methods (cf., for example, Bull. Korean Chem. Soc. 2000, 21, 165-166; Chem. Pharm. Bull. 1992, 40, 240-4; JP 9-132567).

Using, for example, N-(2-iodophenyl)-3-methyl-2-thiophenecarboxamides and 3-chloro-4-fluorophenylboronic acid as starting materials and a catalyst and a base, the course of the process (b) according to the invention can be illustrated by the formula scheme below:

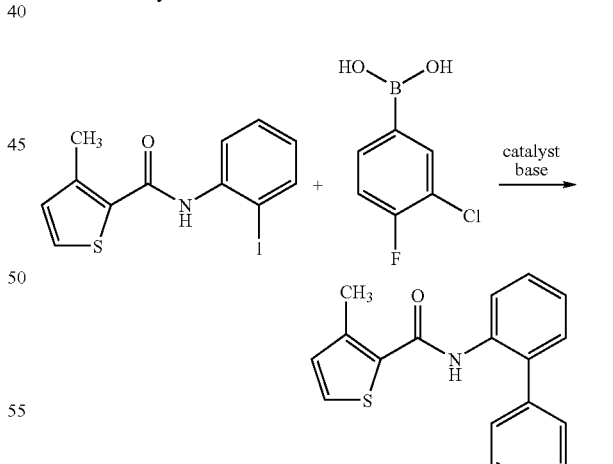

The formula (IV) provides a general definition of the methylthiophenecarboxhaloanilides required as starting materials for carrying out the process (b) according to the invention. In this formula (IV), R$^1$ and R$^2$ preferably or particularly preferably have those meanings which have already been mentioned in connection with the description of the compounds of the formula (I) according to the invention as being preferred or particularly preferred for these radicals. $X^2$ preferably represents bromine or iodine.

The methylthiophenecarboxhaloanilides of the formula (IV) have hitherto not been disclosed. They are novel chemical compounds and also form part of the subject-matter of the present application. They are obtained by c) reacting methylthiophenecarbonyl halides of the formula (II)

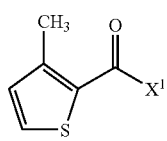

(II)

in which $X^1$ represents halogen, with 2-bromoaniline or 2-iodoaniline, if appropriate in the presence of an acid binder and if appropriate in the presence of a diluent.

The methylthiophenecarbonyl halides of the formula (II) required as starting materials for carrying out the process (c) according to the invention have already been described above, in connection with the process (a) according to the invention.

The substances 2-bromoaniline and 2-iodoaniline furthermore required as starting materials for carrying out the process (c) according to the invention are known chemicals for synthesis.

The formula (V) provides a general definition of the boronic acids furthermore required as starting materials for carrying out the process (b) according to the invention. In this formula (V), $R^3$, $R^4$, $R^5$ and $R^6$ preferably or particularly preferably have those meanings which have already been mentioned in connection with the description of the compounds of the formula (I) according to the invention as being preferred or particularly preferred for these radicals.

Boronic acids of the formula (V) are known chemicals for synthesis. They can also be prepared immediately prior to the reaction directly from halobenzene derivatives and boronic acid esters and be reacted further without work-up (see also the Preparation Examples).

Suitable diluents for carrying out processes (a) and (c) according to the invention are all inert organic solvents. These preferably include aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol, or amides, such as N,N-dimethylformamide, N,N-dimethylacetamide, N-methylformanilide, N-methylpyrrolidone or hexamethylphosphoric triamide.

If appropriate, the processes (a) and (c) according to the invention are carried out in the presence of a suitable acid acceptor. Suitable acid acceptors are all customary inorganic or organic bases. These include, preferably, alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethyl aminopyridine, diazabicyclooctane (DABCO), diazabicyclononene (DBN) or diazabicycloundecene (DBU).

When carrying out the processes (a) and (c) according to the invention, the reaction temperatures can be varied within a relatively wide range. In general, the processes are carried out at temperatures of from 0° C. to 150° C., preferably at temperatures of from 20° C. to 110° C.

For carrying out the process (a) according to the invention for preparing compounds of the formula (I), in general from 0.2 to 5 mol, preferably from 0.5 to 2 mol, of aniline derivative of the formula (III) are employed per mole of the methylthiophenecarbonyl halide of the formula (II).

For carrying out the process (c) according to the invention for preparing compounds of the formula (IV), in general from 0.2 to 5 mol, preferably from 0.5 to 2 mol, of 2-bromoaniline or 2-iodoaniline are employed per mole of the methylthiophenecarbonyl halide of the formula (II).

Suitable diluents for carrying out the process (b) according to the invention are all inert organic solvents. These preferably include aliphatic, alicyclic or aromatic hydrocarbons, such as, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, s- or t-butanol, ethanediol, propane-1,2-diol, ethoxyethanol, methoxyethanol, diethylene glycol monomethyl ether, diethylene glycol monoethyl ether, mixtures thereof with water or pure water.

When carrying out the process (b) according to the invention, the reaction temperatures can be varied within a relatively wide range. In general, the process is carried out at temperatures of from 0° C. to 150° C., preferably at temperatures of from 20° to 110° C.

The process (b) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N- dimethylaminopyridine, diazabicyclooctane (DABCO), diazabicyclononene (DBN) or diazabicycloundecene (DBU).

The process (b) according to the invention is carried out in the presence of a catalyst, such as, for example, a palladium salt or complex. Suitable for this purpose are, preferably, palladium chloride, palladium acetate, tetrakis (triphenyl-phosphine)palladium, bis(triphenylphosphine) palladium dichloride or 1,1'-bis(di-phenylphosphino)ferrocenepalladium(II) chloride.

It is also possible to generate a palladium complex in the reaction mixture by separate addition of a palladium salt and a complex ligand, such as, for example, triethyl-phosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenyl)-phosphine, 2,2'-bis(diphenylphosphine)-1,1'-binaphthyl, 1,4-bis(diphenylphosphine)butane, 1,2-bis(diphenylphosphine)ethane, 1,4-bis(dicyclohexylphosphine) butane, 1,2-bis(di-cyclohexylphosphine)ethane, 2-(dicyclohexylphosphine)-2'-(N,N-dimethylamino)-biphenyl, bis(diphenylphosphino)ferrocene or tris-(2,4-tert-butylphenyl)phosphite to the reaction.

For carrying out the process (b) according to the invention for preparing the compounds of the formula (I), in general from 1 to 15 mol, preferably from 2 to 8 mol, of the boronic acid of the formula (V) are employed per mole of the methylthiophenecarboxhaloanilide of the formula (IV).

The processes (a), (b) and (c) according to the invention are generally carried out under atmospheric pressure. However, it is also possible to operate under elevated or reduced pressure—in general between 0.1 bar and 10 bar.

The substances according to the invention have potent microbicidal activity and can be employed for controlling undesirable micro-organisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium;*

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;* and

*Pseudocercosporella* species, such as, for example, *Pseudocercosporella herpotrichoides.*

The active compounds according to the invention also show a strong invigorating action in plants. Accordingly, they are suitable for mobilizing the internal defences of the plant against attack by unwanted micro-organisms.

In the present context, plant-invigorating (resistance-inducing) compounds are to be understood as meaning substances which are capable of stimulating the defence system of plants such that, when the treated plants are subsequently inoculated with unwanted micro-organisms, they develop substantial resistance to these micro-organisms.

In the present case, unwanted micro-organisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed with particularly good results for controlling cereal diseases, such as, for example, against *Pyrenophora* species, diseases in viticulture, fruit and vegetable cultivation, such as, for example, against *Venturia, Sphaerotheca* and *Podosphaera* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on, injecting and, in the case of propagation material, in particular in the case of seeds, furthermore by one- or multi-layer coating.

In the protection of materials, the compounds according to the invention can be employed for protecting industrial materials against infection with, and destruction by, undesired micro-organisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, micro-organisms. Parts of production plants, for example cooling-water circuits, which may be impaired by the proliferation of micro-organisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Micro-organisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Micro-organisms of the following genera may be mentioned as examples:
*Alternaria*, such as *Alternaria tenuis,*
*Aspergillus*, such as *Aspergillus niger,*
*Chaetomium*, such as *Chaetomium globosum,*
*Coniophoras*, such as *Coniophora puetana,*
*Lentinus*, such as *Lentinus tigrinus,*
*Penicillium*, such as *Penicillium glaucum,*
*Polyporus*, such as *Polyporus versicolor,*
*Aureobasidium*, such as *Aureobasidium pullulans,*
*Sclerophoma*, such as *Sclerophoma pityophila,*
*Trichoderma*, such as *Trichoderma viride,*
*Escherichia*, such as *Escherichia coli,*
*Pseudomonas*, such as *Pseudomonas aeruginosa*, and
*Staphylococcus*, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, aryl-sulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:
2-phenylphenol; 8-hydroxyquinolin sulphate;
acibenzolar-S-methyl; aldimorph; amidoflumet; ampropylfos; ampropylfos-potassium; andoprim; anilazine; azaconazole; azoxystrobin;
benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine;
calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;
Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;
edifenphos; epoxiconazole; ethaboxam; ethirimol; etridiazole;
famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox;
guazatine; hexachlorobenzene; hexaconazole; hymexazole;
imazalil; imibenconazole; iminoctadine triacetate; iminoctadine tris(albesil); iodocarb; ipconazole; iprobenfos; iprodione; iprovalicarb; irumamycin; isoprothiolane; isovaledione;
kasugamycin; kresoxim-methyl;
mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin;
natamycin; nicobifen; nitrothal-isopropyl; noviflumuron; nuarimol;
ofurace; orysastrobin; oxadixyl; oxolinic acid; oxpoconazole; oxycarboxin; oxyfenthiin;
paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole pyraclostrobin; pyrazophos; pyrifenox; pyrimethanil; pyroquilon; pyroxyfur; pyrrolenitrine;
quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;
uniconazole; validamycin A; vinclozolin; zineb; ziram; zoxamide;
(2S)-N-[2-[4-[[3-(4-chlorophenyl)-2-propynyl]oxy]-3-methoxyphenyl]ethyl]-3-methyl-2-[(methylsulphonyl)amino]butanamide;
1-(1-naphthalenyl)-1H-pyrrole-2,5-dione;
2,3,5,6-tetrachloro-4-(methylsulphonyl)pyridine;
2-amino-4-methyl-N-phenyl-5-thiazolecarboxamide;
2-chloro-N-(2,3-dihydro-1,1,3-trimethyl-1H-inden-4-yl)-3-pyridinecarboxamide;
3,4,5-trichloro-2,6-pyridinedicarbonitrile;
actinovate; cis-1-(4-chlorophenyl)-2-(1H-1,2,4-triazol-1-yl) cycloheptanol;
methyl 1-(2,3-dihydro-2,2-dimethyl-1H-inden-1-yl)-1H-imidazole-5-carboxylate;
monopotassium carbonate; N-(6-methoxy-3-pyridinyl)-cyclopropanecarboxamide;
N-butyl-8-(1,1-dimethylethyl)-1-oxaspiro[4.5]decane-3-amine;
sodium tetrathiocarbonate;
and copper salts and preparations, such as Bordeaux mixture; copper hydroxide; copper naphthenate; copper oxychloride; copper sulphate; cufraneb; copper oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azin-phos-ethyl, azocyclotin,

*Bacillus popilliae*, *Bacillus sphaericus*, *Bacillus subtilis*, *Bacillus thuringiensis*, *Bacillus thuringiensis* strain EG-2348, *Bacillus thuringiensis* strain GC-91, *Bacillus thuringiensis* strain NCTC-11821, baculoviruses, *Beauveria bassiana*, *Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentylisomer, bioethanomethrin, biopermethrin, bioresmethrin, bistrifluron, BPMC, brofenprox, bromophosethyl, bromopropylate, bromfenvinfos (-methyl), BTG-504, BTG-505, bufencarb, buprofezin, butathiofos, butocarboxim, butoxycarboxim, butyl-pyridaben, cadusafos, camphechlor, carbaryl, carbofuran, carbophenothion, carbosulfan, cartap, CGA-50439, chinomethionat, chlordane, chlordimeform, chioethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, trans-fluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GUARD (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

PREPARATION EXAMPLES

Example 1

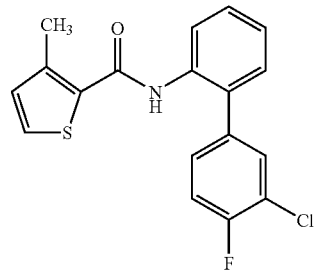

Process (a)

0.36 ml (2.6 mmol) of triethylamine and a solution of 0.25 g (1.56 mmol) of 3-methylthiophene-2-carbonyl chloride in 3 ml of tetrahydrofuran are added to a solution of 0.288 g (1.3 mmol) of 3'-chloro-4'-fluoro-1,1'-biphenyl-2-amine in 3 ml of tetrahydrofuran. The reaction solution is stirred at 60° C. for 16 hours. For work-up, the solution is concentrated and chromatographed on silica gel using cyclohexane/ethyl acetate.

This gives 0.45 g (99% of theory) of N-(3'-chloro-4'-fluoro-1,1'-biphenyl-2-yl)-3-methyl-2-thiophenecarboxamide of logP (pH 2.3)=3.85.

Example 2

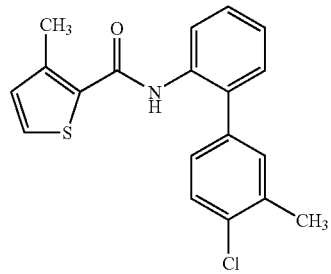

Process (b)

With exclusion of oxygen, 103 mg (0.5 mmol) of 2-chloro-5-bromotoluene, 162 mg (1.65 mmol) of potassium acetate and 152 mg (0.6 mmol) of pinacoldiboronic ester are dissolved in 8 ml of degassed dimethyl sulphoxide, and a catalytic amount (37 mg) of 1,1'-bis(diphenylphosphino)ferrocenepalladium(II)chloride is added. The reaction mixture is stirred at 80-90° C. for 2 hours. After cooling, 1.25 ml of a 2 molar solution of sodium carbonate, a solution of 148 mg (0.5 mmol) of N-(2-bromophenyl)-3-methyl-2-thiophenecarboxamide in 4 ml of dimethyl sulfoxide and a further 37 mg of 1,1'-bis(diphenylphosphino)ferrocenepalladium(II)chloride are added to the reaction mixture, and the mixture is stirred at 80-90° C. for another 16 hours. For work-up, 2 ml of water and 8 ml of ethyl acetate are added and the organic phase is separated off. The organic phase is concentrated and filtered through activated carbon and silicic acid. The filtrate is chromatographed on silica gel using cyclohexane/ethyl acetate (1:1).

This gives 79 mg (46% of theory) of N-(3'-chloro-4'-methyl-1,1'-biphenyl-2-yl)-3-methyl-2-thiophenecarboxamide having a logP (pH 2.3)=4.41.

The compounds of the formula (I) listed in Table 1 below are obtained analogously to Examples 1 and 2 and in accordance with the statements in the general descriptions of processes a) and b).

TABLE 1

I)

| Ex. | $R^1$ | $R^2$ | $R^3$ | $R^4$ | $R^5$ | $R^6$ | logP |
|---|---|---|---|---|---|---|---|
| 3 | H | H | H | H | Br | H | 4.12 |
| 4 | H | H | H | H | $CF_3$ | H | 4.06 |
| 5 | H | H | H | Cl | H | H | 3.97 |
| 6 | H | H | H | H | $OCF_3$ | H | 4.33 |
| 7 | H | H | H | H | $SCH_3$ | H | 4.03 |
| 8 | H | H | H | H | F | H | 3.65 |
| 9 | H | H | H | F | F | H | 3.55 |
| 10 | H | H | H | F | Cl | H | 3.85 |
| 11 | H | H | H | F | $OCF_3$ | H | 4.13 |
| 12 | H | H | H | $CF_3$ | $OCF_3$ | H | 4.37 |
| 13 | H | H | H | Cl | Cl | H | 4.18 |
| 14 | H | H | H | $CF_3$ | F | H | 3.85 |
| 15 | H | H | H | Cl | H | Cl | 4.32 |
| 16 | H | H | F | H | F | H | 3.41 |
| 17 | H | H | H | $CF_3$ | Cl | H | 4.13 |
| 18 | H | H | H | $CF_3$ | $CH_3$ | H | 4.27 |
| 19 | H | H | Cl | H | Cl | H | 5.76 |
| 20 | H | H | $CH_3$ | H | Cl | H | 4.51 |
| 21 | H | H | F | H | Cl | H | 3.75 |
| 22 | F | H | H | Cl | Cl | H | 3.71 |
| 23 | H | F | H | Cl | Cl | H | 4.10 |
| 24 | H | H | H | H | Cl | H | 3.87 |
| 25 | H | H | H | H | CN | H | 2.85 |
| 26 | H | H | H | F | $CF_3$ | H | 3.85 |
| 27 | H | H | H | $CH_3$ | F | H | 3.99 |
| 28 | H | H | H | F | H | F | 3.50 |
| 29 | H | H | H | H | I | H | 4.16 |
| 30 | H | H | H | F | $CH_3$ | H | 3.94 |
| 31 | H | H | H | Cl | $CH_3$ | H | 4.29 |
| 32 | H | H | F | H | $CH_3$ | H | 3.79 |
| 33 | H | H | H | Cl | $CF_3$ | H | 4.09 |

Preparation of Starting Materials of the Formula (II)

Example (II-1)

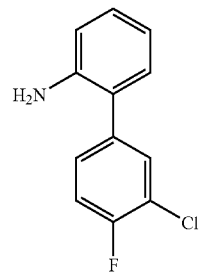

38.8 g (223 mmol) of 3-chloro-4-fluorophenylboronic acid and 40.6 g (186 mmol) of 2-iodoaniline are, under argon, dissolved in 220 ml of toluene, 22 ml of ethanol and 45 ml of a 4 M solution of sodium bicarbonate. 4.3 g (4 mmol) of tetrakis(triphenyl-phosphine)palladium(0) are added, and the reaction solution is stirred at 80° C. under argon for 16 hours. The organic phase is separated off, dried over magnesium sulphate and concentrated. The residue is chromatographed on silica gel using cyclohexane/ethyl acetate.

This gives 22.5 g (48% of theory) of 3'-chloro-4'-fluoro-1,1'-biphenyl-2-amine of logP (pH 2.3)=3.01.

Preparation of Starting Materials of the Formula (III)

Example (III-1)

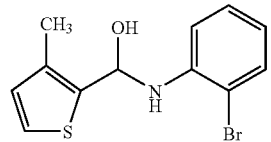

Process (c)

5.6 g (0.040 mol) of potassium carbonate and 6.0 g (0.037 mol) of 3-methylthiophene-2-carbonylchloride are added to a solution of 5.36 g (0.031 mol) of 2-bromoaniline in 80 ml of acetonitrile. The reaction solution is heated under reflux for 16 hours and then filtered and concentrated under reduced pressure. The residue is chromatographed on silica gel using cyclohexan/ethyl acetate (2:1).

This gives 7.4 g (80% of theory) of N-(2-bromophenyl)-3-methyl-2-thiophenecarboxamide of logP (pH 2.3)=3.30.

The logP value given in the Preparation Examples and tables above are determined in accordance with EEC Directives 79/831 Annex V.A8 by HPLC (High Performance Liquid Chromatography) using a reverse-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

USE EXAMPLES

Example A

*Podosphaera* Test (Apple)/Protective

Solvents: 24.5 parts by weight of acetone
24.5 parts by weight dimethylacetamide
Emulsifier: 1.0 part by weight alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

*Podosphaera* Test (Apple)/protective

| Active compound | | Application rate of active compound in g/ha | Efficacy in % |
|---|---|---|---|
| 5 | 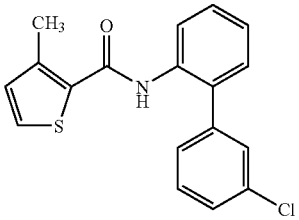 | 100 | 100 |
| 6 | 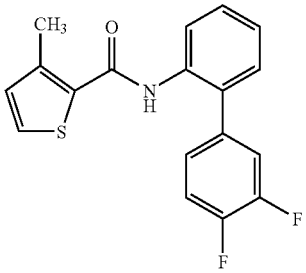 | 100 | 100 |

TABLE A-continued

*Podosphaera* Test (Apple)/protective

| Active compound | | Application rate of active compound in g/ha | Efficacy in % |
|---|---|---|---|
| 9 | 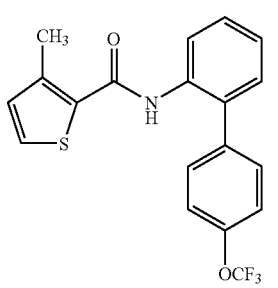 | 100 | 100 |
| 10 | 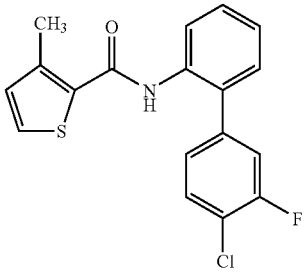 | 100 | 100 |
| 1 | 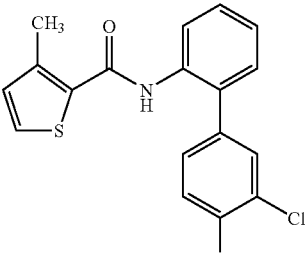 | 100 | 100 |
| 11 | 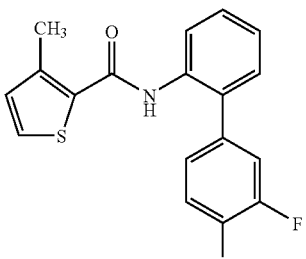 | 100 | 100 |
| 12 | 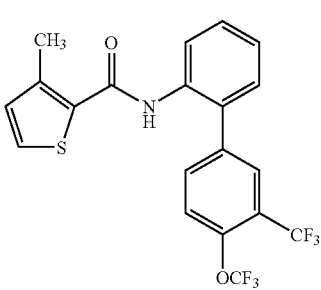 | 100 | 100 |

TABLE A-continued

Podosphaera Test (Apple)/protective

| Active compound | Application rate of active compound in g/ha | Efficacy in % |
|---|---|---|
| 2 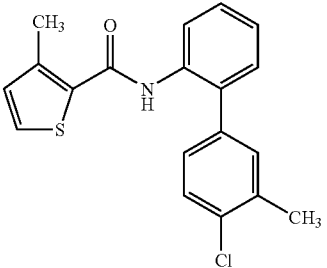 | 100 | 100 |
| 15 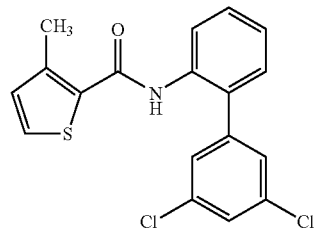 | 100 | 100 |
| 19 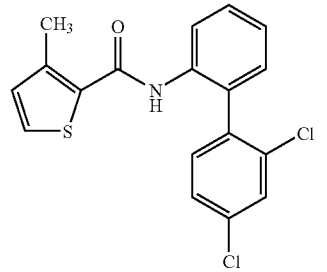 | 100 | 100 |
| 13 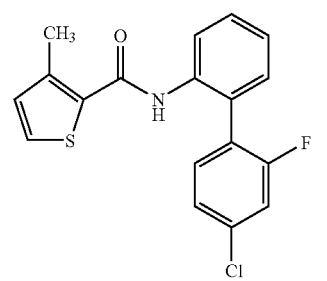 | 100 | 100 |

Example B

Sphaerotheca Test (Cucumber)/Protective
Solvents: 24.5 parts by weight of acetone
24.5 parts by weight dimethylacetamide
Emulsifier: 1.0 part by weight alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Sphaerotheca fuliginea. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE B

Sphaerotheca Test (cucumber)/protective

| Active compound | Application rate of active compound in g/ha | Efficacy in % |
|---|---|---|
| 5 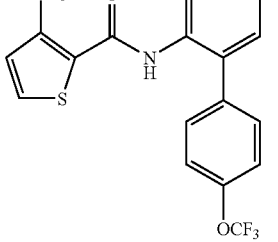 | 100 | 93 |
| 6 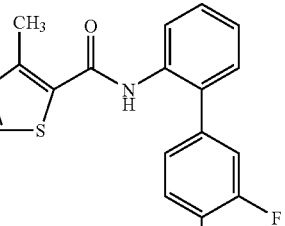 | 100 | 100 |
| 9 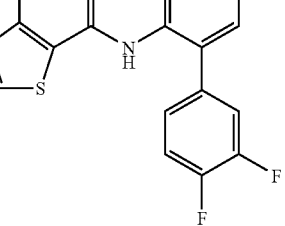 | 100 | 100 |
| 10 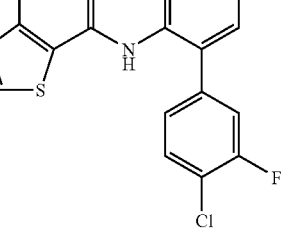 | 100 | 100 |

TABLE B-continued

*Sphaerotheca* Test (cucumber)/protective

| Active compound | Application rate of active compound in g/ha | Efficacy in % |
|---|---|---|
| 1 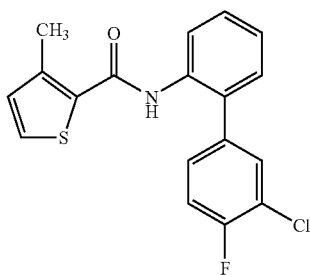 | 100 | 100 |
| 11 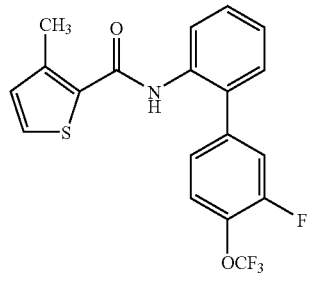 | 100 | 100 |
| 12 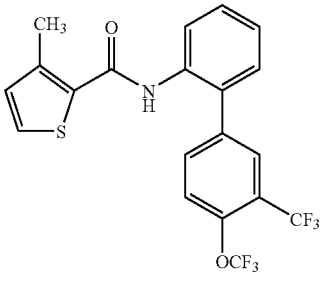 | 100 | 100 |
| 15 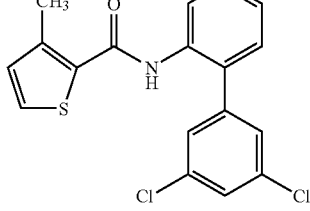 | 100 | 100 |
| 19 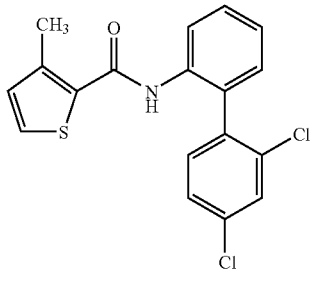 | 100 | 96 |

TABLE B-continued

*Sphaerotheca* Test (cucumber)/protective

| Active compound | Application rate of active compound in g/ha | Efficacy in % |
|---|---|---|
| 13 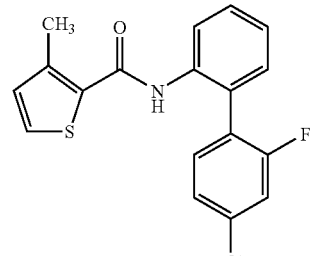 | 100 | 100 |

Example C

*Venturia* Test (Apple)/Protective

Solvents: 24.5 parts by weight acetone
24.5 parts by weight dimethylacetamide
Emulsifier: 1.0 part by weight alkylaryl polyglycol ether To produce a suitable preparation of the active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous Conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

*Venturia* Test (Apple)/protective

| Active compound | Application rate of active compound in g/ha | Efficacy in % |
|---|---|---|
| 5 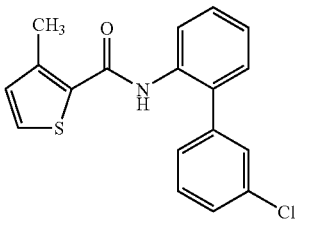 | 100 | 100 |

TABLE C-continued

Venturia Test (Apple)/protective

| | Active compound | Application rate of active compound in g/ha | Efficacy in % |
|---|---|---|---|
| 9 | 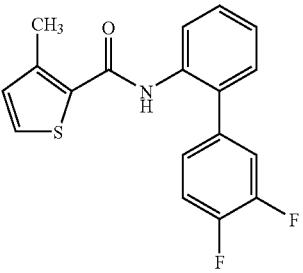 | 100 | 100 |
| 10 | 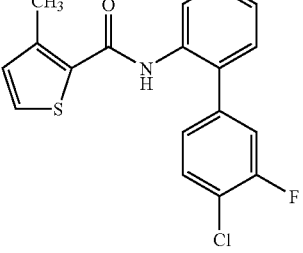 | 100 | 100 |
| 1 | 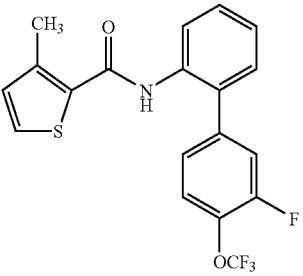 | 100 | 100 |
| 11 | 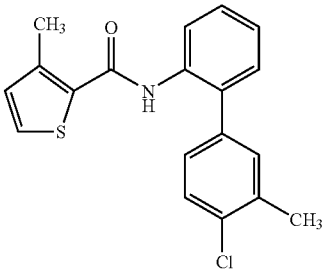 | 100 | 100 |
| 2 | 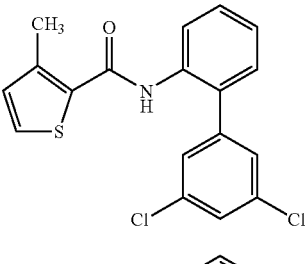 | 100 | 100 |
| 15 | 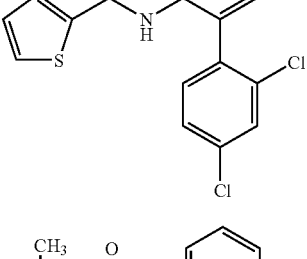 | 100 | 97 |
| 19 | 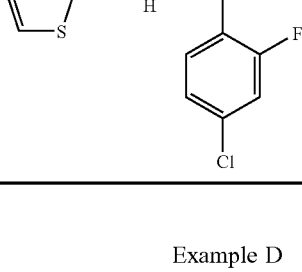 | 100 | 99 |
| 13 | 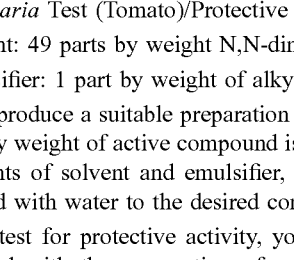 | 100 | 100 |

Example D

*Alternaria* Test (Tomato)/Protective

Solvent: 49 parts by weight N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and then remain at 100% relative humidity and 20° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

*Alternaria* Test (Tomato)/protective

| Active compound | Application rate of active compound in g/ha | Efficacy in % |
|---|---|---|
| 3 (3-methylthiophene-2-carboxamide with 4'-bromobiphenyl-2-yl) | 750 | 100 |
| 5 (3-methylthiophene-2-carboxamide with 3'-chlorobiphenyl-2-yl) | 750 | 100 |
| 6 (3-methylthiophene-2-carboxamide with 4'-trifluoromethoxybiphenyl-2-yl) | 750 | 100 |
| 8 (3-methylthiophene-2-carboxamide with 4'-fluorobiphenyl-2-yl) | 750 | 100 |
| 9 (3-methylthiophene-2-carboxamide with 3',4'-difluorobiphenyl-2-yl) | 750 | 100 |
| 10 (3-methylthiophene-2-carboxamide with 4'-chloro-3'-fluorobiphenyl-2-yl) | 750 | 100 |

Example E

*Pyrenophora teres* Test (Barley)/Protective
Solvent: 25 parts by weight N,N-dimethylacetamide
Emulsifier: 0.6 part by weight alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of about 20° C. and relative atmospheric humidity of about 80%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE E

*Pyrenophora teres* Test (barley)/protective

| Active compound | Application rate of active compound in g/ha | Efficacy in % |
|---|---|---|
| 8 (3-methylthiophene-2-carboxamide with 4'-fluorobiphenyl-2-yl) | 500 | 80 |

TABLE E-continued

Pyrenophora teres Test (barley)/protective

| Active compound | Application rate of active compound in g/ha | Efficacy in % |
|---|---|---|
| 9 (3-methyl-thiophene-2-carboxamide with 3',4'-difluorobiphenyl-2-yl) | 500 | 100 |
| 13 (3-methyl-thiophene-2-carboxamide with 3',4'-dichlorobiphenyl-2-yl) | 500 | 94 |

What is claimed is:

1. A methylthiophenecarboxanilide of formula (I)

(I) [structure of 3-methylthiophene-2-carboxamide N-linked to biphenyl with R¹, R², R³, R⁴, R⁵, R⁶ substituents]

in which
R$^1$ and R$^2$ are identical or different and independently of one another represent hydrogen or fluorine,
R$^3$, R$^4$, and R$^6$ are identical or different and independently of one another represent hydrogen, halogen, C$_1$-C$_6$-alkyl, or C$_1$-C$_4$-haloalkyl having 1 to 5 halogen atoms,
R$^5$ represents hydrogen, halogen, cyano, nitro, C$_1$-C$_6$-alkyl, C$_2$-C$_6$-alkenyl, C$_3$-C$_6$-cycloalkyl, C$_1$-C$_4$-alkoxy, C$_1$-C$_4$-alkylthio, C$_1$-C$_4$-alkylsulfonyl, C$_1$-C$_4$-haloalkyl having 1 to 5 halogen atoms, C$_1$-C$_4$-haloalkoxy having 1 to 5 halogen atoms, C$_1$-C$_4$-haloalkylthio having 1 to 5 halogen atoms, or C$_1$-C$_4$-haloalkylsulfonyl having 1 to 5 halogen atoms,
with the proviso that R$^3$, R$^4$, R$^5$, and R$^6$ do not simultaneously represent hydrogen.

2. A methylthiophenecarboxanilide of formula (I) according to claim 1 in which
R$^1$ and R$^2$ are identical or different and independently of one another represent hydrogen or fluorine,
R$^3$, R$^4$, and R$^6$ are identical or different and independently of one another represent hydrogen, fluorine, chlorine, bromine, iodine, methyl, ethyl, n- or i-propyl, n-, i-, s-, or t-butyl, trifluoromethyl, trichloromethyl, or trifluoroethyl,
R$^5$ represents hydrogen, fluorine, chlorine, bromine, iodine, cyano, nitro, methyl, ethyl, n- or i-propyl, n-, i-, s-, or t-butyl, cyclopropyl, methoxy, ethoxy, methylthio, ethylthio, n- or i-propylthio, trifluoromethyl, trichloromethyl, trifluoroethyl, difluoromethoxy, trifluoromethoxy, difluorochloromethoxy, trifluoroethoxy, difluoromethylthio, difluorochloromethylthio, or trifluoromethylthio,
with the proviso that R$^3$, R$^4$, R$^5$, and R$^6$ do not simultaneously represent hydrogen.

3. A methylthiophenecarboxanilide of formula (I) according to claim 1 in which
R$^1$ and R$^2$ are identical or different and independently of one another represent hydrogen or fluorine,
R$^3$, R$^4$, and R$^6$ are identical or different and independently of one another represent hydrogen, fluorine, chlorine, bromine, iodine, methyl, or trifluoromethyl,
R$^5$ represents hydrogen, fluorine, chlorine, bromine, iodine, cyano, methyl, cyclopropyl, methoxy, methylthio, trifluoromethyl, trichloromethyl, trifluoroethyl, difluoromethoxy, trifluoromethoxy, difluorochloromethoxy, trifluoroethoxy, difluoromethylthio, difluorochloromethylthio, or trifluoromethylthio,
with the proviso that R$^3$, R$^4$, R$^5$, and R$^6$ do not simultaneously represent hydrogen.

4. A process for preparing a methylthiophenecarboxanilide of formula (I) according to claim 1 comprising
(a) reacting a methylthiophenecarbonyl halide of formula (II)

(II) [structure of 3-methylthiophene-2-carbonyl halide, with X$^1$]

in which X$^1$ represents halogen,
with an aniline derivative of formula (III)

(III) [structure of 2-amino biphenyl with R¹-R⁶ substituents]

in which R$^1$, R$^2$, R$^3$, R$^4$, R$^5$, and R$^6$ are as defined for formula (I) in claim 1,
optionally in the presence of an acid binder and optionally in the presence of a diluent, or
(b) reacting a methylthiophenecarboxhalogenanilide of formula (IV)

(IV) [structure with X$^2$]

in which $R^1$ and $R^2$ are as defined for formula (I) in claim 1, and $X^2$ represents bromine or iodine, with a boronic acid of formula (V)

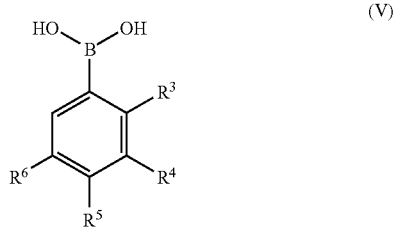

(V)

in which $R^3$, $R^4$, $R^5$, and $R^6$ are as defined for formula (I) in claim 1, in the presence of a catalyst, optionally in the presence of an acid binder, and optionally in the presence of a diluent.

5. A composition for controlling unwanted micro-organisms comprising one or more methylthiophenecarboxanilides of formula (I) according to claim 1 and one or more extenders and/or surfactants.

6. A method for controlling unwanted micro-organisms comprising applying an effective amount of a methylthiophenecarboxanilide of formula (I) according to claim 1 to the micro-organisms and/or their habitat.

7. A method for preparing compositions for controlling unwanted micro-organisms comprising mixing one or more methylthiophenecarboxanilides of formula (I) according to claim 1 with one or more extenders and/or surfactants.

\* \* \* \* \*